United States Patent
Lowell

(10) Patent No.: US 8,349,372 B1
(45) Date of Patent: Jan. 8, 2013

(54) COMPOSITION FOR THE PREVENTION AND TREATMENTS OF ACNE AND OILY SKIN

(76) Inventor: Seth Lowell, Quakertown, PA (US)

( * ) Notice: Subject to any disclaimer, the term of this patent is extended or adjusted under 35 U.S.C. 154(b) by 0 days.

(21) Appl. No.: 13/046,741

(22) Filed: Mar. 12, 2011

Related U.S. Application Data

(60) Provisional application No. 61/313,465, filed on Mar. 12, 2010.

(51) Int. Cl.
*A61K 36/00* (2006.01)
*A61K 36/752* (2006.01)
(52) U.S. Cl. .............. 424/725; 424/736
(58) Field of Classification Search .......... None
See application file for complete search history.

(56) References Cited

U.S. PATENT DOCUMENTS

| 2006/0263440 A1* | 11/2006 | Cecil | 424/539 |
| 2011/0129552 A1* | 6/2011 | Saha et al. | 424/725 |

FOREIGN PATENT DOCUMENTS

| CN | 1346665 A | * | 5/2002 |
| JP | 2008031049 A | * | 2/2008 |

* cited by examiner

*Primary Examiner* — Qiuwen Mi
(74) *Attorney, Agent, or Firm* — H. John Rizvi; Glenn E. Gold; Gold & Rizvi, P.A.

(57) ABSTRACT

A skin blemish and acne treatment composition is manufacturing by mixing together a predetermined volume of dishwashing soap having natural ingredient, a predetermined volume of tea tree oil, and a predetermined volume of witch hazel. The composition is utilized as a body wash for the treatment and prevention of blemished skin, acne and oily skin. The dishwashing soap can be manufactured using any of a variety of natural ingredients.

18 Claims, 2 Drawing Sheets

COMPOSITION FOR THE PREVENTION AND TREATMENTS OF ACNE AND OILY SKIN

CROSS-REFERENCE TO RELATED APPLICATION

This Non-Provisional Utility application claims the benefit of co-pending U.S. Provisional Patent Application Ser. No. 61/313,465, filed on Mar. 12, 2010, which is incorporated herein in its entirety.

FIELD OF THE INVENTION

The present invention relates generally to a composition useful for fighting against skin blemishes. The invention is, however, more particularly directed to a composition for the prevention of acne and oily skin, basically blemishes created due to the use of sport supplements and working out in the gym.

BACKGROUND OF THE INVENTION

Skin is the largest organ of the human body. Skin does not just cover the body; it functions as a protective wrapping. Along with a layer of fat underneath, it insulates the body against all kinds of bumps, bangs and wears and tears. It keeps germs and water out and keeps the body's fluids and salts in.

The art of beauty has existed since ancient times, with rituals focused on cleanliness, beauty and the use of primitive cosmetics. Modern science and innovation have prompted an array of treatments and prevention techniques to reduce the effects of different skin blemishes, including acne and oily skin. New treatments are constantly on the horizon. While these new treatments may offer some promise, more human studies need to be done to reveal the duration and degree of effects.

From all the different blemishes that affect the human skin, acne is one that affects the aesthetic of almost every type of person, young and adult, very seriously. Acne is a skin condition that causes whiteheads, blackheads, and inflamed red lesions (papules, pustules, and cysts) to form. These growths are commonly called pimples or "zits." Acne occurs when tiny holes on the surface of the skin, called pores, become clogged. Each pore is an opening to a canal called a follicle, which contains a hair and an oil gland. Normally, the oil glands help keeps the skin lubricated and help remove old skin cells. When glands produce too much oil, the pores can become blocked, accumulating dirt, debris, and bacteria.

Another important aesthetic problem is created by oily skin. The source of all the trouble is the microscopic sebaceous gland, safely hidden beneath the surface of the skin. Sebaceous glands are part of the pilo-sebaceous unit (hair+oil gland duo). These glands lie deep within the dermis. They connect with the hair shaft and empty their contents onto the surface of the skin through the pores. All skin surfaces, except for the palms and soles, possess sebaceous glands. The area with the most oil-producing ability is the one most crowded with sebaceous glands—it's the notorious T-zone (forehead, nose and chin).

Sebaceous glands produce sebum, a complex blend of varied lipids (an assortment of fats), and dead sebaceous gland cells, (the cells that manufacture the sebum). Fats found in sebum include triglycerides, wax monoesters, squalane and free fatty acids. And these sebum-based substances affect the general appearance of the skin. Skin and hair no longer look healthy, but instead, greasy, slick and even dirty.

There are several solutions for these problems. For example, for treating acne, there are several expensive creams, ointments and pills among others. Today, virtually every case of acne can be resolved. The key to healing and eliminating acne lesions lies in knowing that treatment takes time. What works for one person may not work for another, and a dermatologist's diagnosis and treatment may be required.

One well-known product for treating acne is a series of products manufactured by Guthy-Renker of Palm Desert, Calif., and commercialized under a PROACTIV brand. The brand offering and treatment comprises three different products. The first product is a cleanser made with micro-crystal benzoyl peroxide, featuring smaller, finer particles designed to quickly penetrate pores to start killing acne-causing bacteria on contact. Tiny exfoliating beads gently remove dirt, excess oil and dead skin cells to help keep pores from clogging. The second product is a revitalizing and refreshing, alcohol-free toner that helps remove impurities and excess oil so your skin looks and feels clean, soft and refreshed—not tight and dried out. The last one is a repairing lotion that gets deep into clogged pores faster but is designed to be gentler on the skin. It's an oil-free formula that's safe for the entire face.

Furthermore, for treating oily skin, there are different solutions. For example, one way is with proper cleansing. However, there are some extra things to do, for example, apply an astringent or a toner after cleansing, treat your oily skin to a clay mask or exfoliate your skin once or twice a week.

Even though the above cited treatments and methods for the prevention and treatment of skin blemishes address some of the needs of the market, a natural and economical composition for treating skin blemishes due to sport supplements and time spent working out in the gym or any place of activity is still desired.

SUMMARY OF THE INVENTION

The basic inventive composition is directed towards a composition for use in a shower to fight acne and oily skin. Know causes of acne and oily skin include sport supplements and time spent working out in the gym.

In a first exemplary embodiment of the skin blemish and acne treatment composition, the composition comprises a combination of ingredients including dishwashing soap, tea tree oil and witch hazel.

In the first exemplary embodiment, the preferred volumes of ingredients are as follows:
  a. Dishwashing soap, comprising a volume between 85% and 99.8%
  b. Tea tree oil, comprising a volume between 0.1% and 5.0%
  c. Witch Hazel, comprising a volume between 0.1% and 10.0%

In a modified exemplary embodiment, the preferred volumes of ingredients are as follows:
  a. Dishwashing soap, comprising a volume between 94% and 99.4%
  b. Tea tree oil, comprising a volume between 0.1% and 1.0%
  c. Witch Hazel, comprising a volume between 0.5% and 5.0%

In another aspect, an exemplary ingredient list of the skin blemish and acne treatment composition can further comprise (percentages by volume):
  a. Castile soap, comprising 5% to 15% of the total content;
  b. Warm water, comprising 5% to 15% of the total content;
  c. Tea tree oil, comprising 5% to 15% of the total content;

d. Fresh lemon juice, comprising 5% to 15% of the total content; and e. White vinegar, comprising 5% to 15% of the total content;

In another aspect, the dishwashing soap ingredient comprises all natural ingredients, including at least a portion of the following ingredients:

a. Oxygen chlorine-free bleach,
b. Plant-based non-ionic tension-active surfactants,
c. Enzymes,
d. Salts,
e. Silicate,
f. Citrate,
g. Polypeptides,
h. Plant based bleach activator, and
i. Plant based fragrance.

In another aspect, the dishwashing soap ingredient comprises all natural ingredients, including at least a portion of the following ingredients:

a. Water,
b. Sodium Laureth Sulfate,
c. Lauryl Polyglucose,
d. Sodium Chloride,
e. Citric Acid,
f. Fragrance,
g. Limonene,
h. Hydrolized Wheat Gluten,
i. Aloe Barbadensis Gel,
j. Citral, and
k. 2-bromo-2-nitropropane-1,3-diol.

In another aspect, the dishwashing soap ingredient comprises all natural ingredients, including Grapefruit, Green Tea, and at least a portion of the following active ingredients:

a. Sodium Laureth Sulfate, comprising 5% to 15% of the total content;
b. Alkyl Poly Glycoside C10-16, comprising 5% to 15% of the total content;
c. First Perfume, comprising 0.1% to 1% of the total content;
d. Second Perfume, comprising 0.01% to 0.1% of the total content;
e. Limonene (D-), comprising 0.01% to 0.1% of the total content; and
f. 2-Bromo-2-Nitropropane-1,3-Diol, comprising 0.01% to 0.1% of the total content.

In another aspect, the dishwashing soap ingredient comprises all natural ingredients, including Lemon, Aloe Vera, and at least a portion of the following active ingredients:

a. Sodium Laureth Sulfate;
b. Lauryl Glucoside;
c. First Perfume;
d. Limonene
e. 2-Bromo-2-Nitropropane-1,3-Diol; and
f. Second Perfume.

In another aspect, the dishwashing soap ingredient comprises all natural ingredients, including Lemon, Aloe Vera, and at least a portion of the following active ingredients:

a. Sodium Lauryl Ether Sulfate, comprising 5% to 15% of the total content;
b. Fatty Alcohol Sulfate C10-16, comprising 5% to 15% of the total content;
c. Alkyl Poly Glycoside C10-16, comprising 1% to 5% of the total content;
d. Alkyl Poly Glycoside C8-10, comprising 0.1% to 1% of the total content;
e. Citric Acid, comprising 0.1% to 1% of the total content;
f. Perfume, comprising 0.01% to 0.1% of the total content;
g. Limonene (D-), comprising 0.01% to 0.1% of the total content; and
h. Citral, comprising 0.01% to 0.1% of the total content.

In another aspect, a more active dishwashing soap ingredient comprises all natural ingredients, including Grapefruit, Green Tea, and at least a portion of the following active ingredients:

a. Sodium Laureth Sulfate;
b. Sodium Lauryl Sulfate;
c. Lauryl Glucoside;
d. Capryl Glucoside;
e. Citric Acid;
f. Sorbic Acid;
g. Perfume;
h. Limonene; and
i. Citral.

In yet another aspect, the skin blemish and acne treatment composition works by removing extra oil from the skin, treating small open acne with all natural antiseptics, and by reducing redness without over drying the skin.

In yet another aspect, the skin blemish and acne treatment composition is directed at professional and amateur athletes, bodybuilders, and the like.

In yet another aspect, the skin blemish and acne treatment composition is based on all natural products and is developed for use by adults/athletes with a simple application in during a shower. The skin blemish and acne treatment composition rids the user's skin of extra oil, whereby the extra oil is a result of the use of sport supplements.

In yet another aspect, the skin blemish and acne treatment composition can either compliment or replace prescription acne ingestive and/or topical medications and over the counter acne topical solutions available to the public.

In yet another aspect, an extra strength version of the skin blemish and acne treatment composition can include up to 3 times the amount of tea tree oil compared to the original formula.

In summary, the present invention is related to a composition for the prevention and treatments of acne and oily skin, including oxygen chlorine-free bleach, plant-based non-ionic tension-active surfactants, enzymes, salts, silicate, citrate, polypeptides, plant based bleach activator, plant based fragrance, tea tree oil, and witch hazel.

These and other advantages of the invention will be further understood and appreciated by those skilled in the art by reference to the following written specification and claims.

BRIEF DESCRIPTION OF THE DRAWINGS

The invention will now be described, by way of example, with reference to the accompanying drawings, in which.

Like reference numerals refer to like parts throughout the various views of the drawings.

DETAILED DESCRIPTION OF THE INVENTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Most acne solutions are riddled with chemicals and targeted towards young and adolescent kids. Skin blemishes and acne are also prevalent in bodybuilders, athletes, and the like who ingest sports supplements and exercise frequently. Excess oil is one known cause of skin blemishes and acne on bodybuilders, athletes and the like. Several known sources of the excess oil include sport supplements and/or exercise, such as time spent working out in the gym, sports activities (including running, bicycling, skating, tennis, and the like), physical chores, and the like.

Figure 1:
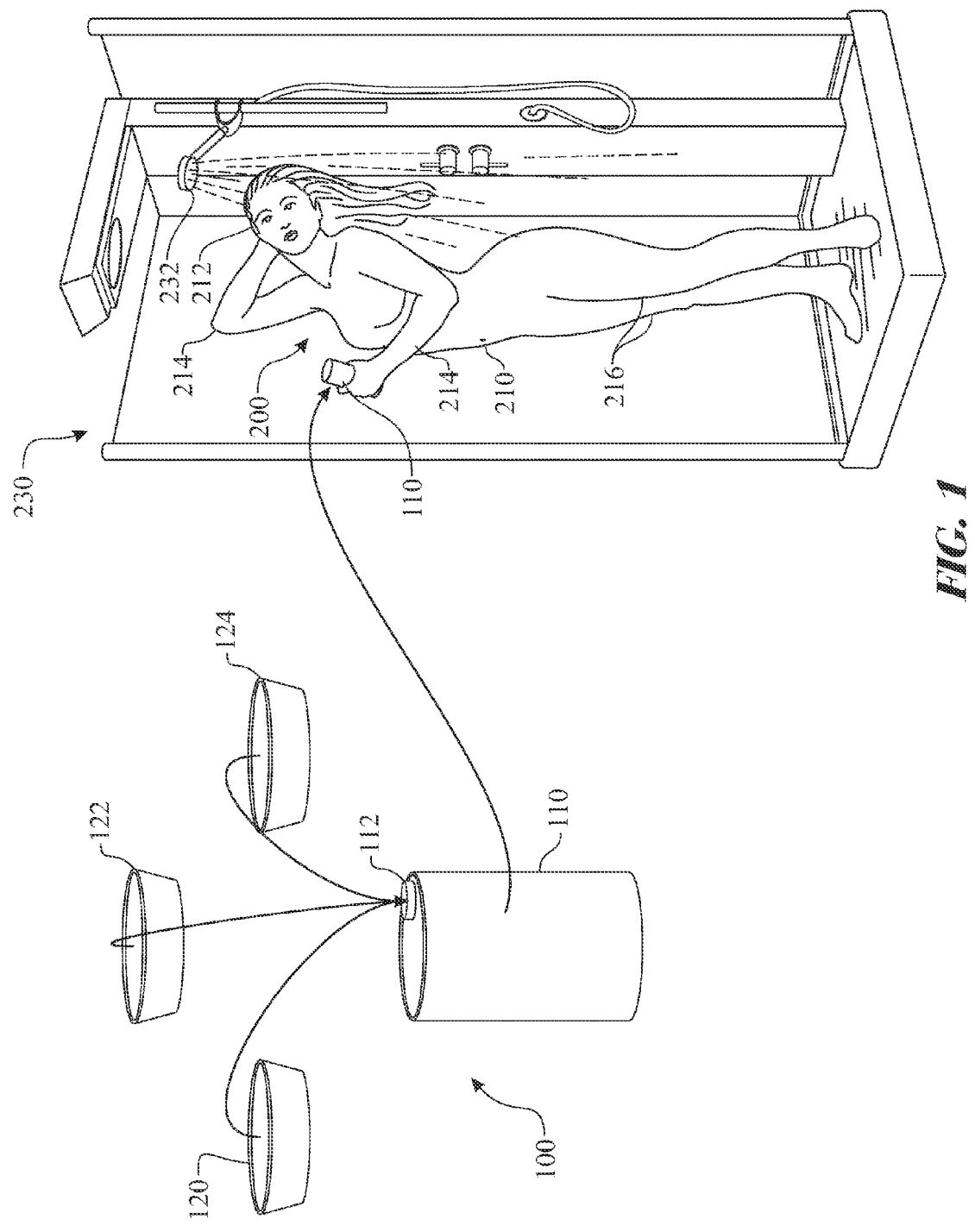
FIG. 1 presents an isometric diagram illustrating a use of a skin blemish and acne treatment composition.

A skin blemish and acne treatment composition 100 is provided to aid in the removal of excess oil from skin of an individual 200 during a shower/bathing process as best illustrated in FIG. 1. The removal of excess oil from skin of an individual 200 is directed towards the treatment of skin blemishes and acne. The exemplary skin blemish and acne treatment composition 100 comprises all natural ingredients. The skin blemish and acne treatment composition 100 is creating by combining a volume of dishwashing soap 120, tea tree oil 122 and witch hazel 124. Dishwashing soap 120 is usually a highly foaming mixture of surfactants with low skin irritation, and is primarily used for hand washing of glasses, plates, cutlery, and cooking utensils in a sink or bowl. The manufacturer determines the detailed ingredients of the dishwashing soap 120, a desired volume of the tea tree oil 122 and a desired volume of the witch hazel 124. The manufacturer can determine the desired volume of tea tree oil 122 and witch hazel 124 to adequately remove excess oil from an individual's skin while not harming the individual 200.

The preferred tea tree oil 122 meets the following criteria. The Australian Standards require that the oil of Melaleuca Alternifolia must be composed of less than 15% Cineole and over 30% Terpinen-4-Ol. The subject "superior" grade of Tea Tree Oil 122 is meticulous analyzed to ensure that if it exceeds these level of Oil Quality Standards decreed by the Australian Government. The desired Tea Tree Oil 122 is composed of less than 5% Cineole and over 35% Terpinen-4-Ol which qualifies for pharmaceutical grade as established by the Australian Tea Tree Oil Industry Association.

The volume of skin blemish and acne treatment composition 100 is packaged in a plurality of composition distribution containers 110. The composition distribution containers 110 can be provided in any desired form factor and size. The composition distribution container 110 includes a container cap 112 providing a resealable feature for storage and removal of the skin blemish and acne treatment composition 100 from the composition distribution container 110.

The individual 200 would obtain the skin blemish and acne treatment composition 100. The individual 200 would bath in a shower 230. Water is discharged from a showerhead 232 and directed towards the individual 200. The individual 200 would apply the skin blemish and acne treatment composition 100 to an individual's body, including, but not limited to the individual's torso 210, an individual's face 212, an individual's arms 214 and an individual's legs 216. The individual's arms 214 and individual's legs 216 can collectively be referred to as the individual's extremities.

TABLE 1

Skin Blemish and Acne Treatment Composition Ingredients
Treatment Composition - Categoric Ingredients

| | | | % Volume | | |
|---|---|---|---|---|---|
| Ingredient | Vol. (ml) | % Volume | Wide Variance | General Variance | Desired Variance |
| Dishwashing Soap | 294 | 98.0 | 70-99.5% | 82.5-99.4% | 92-98.75% |
| Tea Tree Oil | 1.5 | 1.5 | 0.1%-10% | 0.1%-7.5% | 0.25%-3% |
| Witch Hazel | 4.5 | 4.5 | 0.1%-20% | 0.5%-10% | 1.0%-5% |
| Total | 300 | 100.0 | | | |

An enhanced exemplary skin blemish and acne treatment composition 100 comprises the following ingredients:
 a. Liquid Castile Soap;
 b. Warm Water;
 c. Fresh Lemon Juice;
 d. White Vinegar;
 e. Tea Tree Oil 122; and
 f. Witch Hazel 124.

Where the Liquid Castile Soap, Warm Water, Fresh Lemon Juice, and White Vinegar are at least a portion of the ingredients of the dishwashing soap 120.

TABLE 2

Detailed Skin Blemish and Acne Treatment Composition Ingredients
Treatment Composition - Detailed Ingredients

| | | | % Volume | | |
|---|---|---|---|---|---|
| Ingredient | Vol. (ml) | % Volume | Wide Variance | General Variance | Desired Variance |
| Castile Soap | 237 | 47.79 | 15%-80% | 25%-75% | 40%-58% |
| Warm Water | 118 | 23.79 | 15%-35% | 18%-30% | 20%-26% |
| Tea Top Oil | 0.15 | 0.03 | 0.01%-1.0% | 0.01%-0.05% | 0.02%-0.04% |
| Fresh Lemon Juice | 14.8 | 2.98 | 0%-6% | 1.5%-5% | 2.5-3.5% |
| White Vinegar | 118 | 23.79 | 0%-65% | 18%-30% | 20%-26% |
| Tea Top Oil | 0.15 | 0.03 | 0.01%-1.0% | 0.01%-0.05% | 0.02%-0.04% |
| Witch Hazel | 8 | 1.61 | 0.25%-4% | 0.75%-3% | 1.25%-2.25% |
| Total | 496.0 | 100 | | | |

The skin blemish and acne treatment composition 100 is preferably applied while showering for treating common skin blemishes and acne. This provides for removal of excess oils found on the individual's entire body, while reducing redness without over drying the skin. The skin blemish and acne treatment composition 100 is specifically designed to remove excess oil from the skin of the individual. The skin blemish and acne treatment composition 100 is a body surface cleansing product that actively treats full body acne that may be found on the chest, shoulders, back, face, legs, arms, infected hair follicles, etc.

The subject skin blemish and acne treatment composition 100 is considered to be superior to currently available acne medications, as the composition is directed towards full body acne, whereas currently available acne medications are directed towards treatment of facial acne.

A first exemplary dishwashing soap 120 component of the exemplary skin blemish and acne treatment composition 100 comprises the following ingredients:
 a. Water,
 b. Cleaner (Sodium Lauryl Ether Sulfate),
 c. Surfactants (Nonyl Phenols),
 d. Preservative (like Methyl Paraben),
 e. Colorant (Optional),
 f. Foam boosters (Cocodea), and
 g. Thickener (Sodium Chloride).

TABLE 3

Exemplary Dishwashing Soap Ingredients
Dishwashing Soap Ingredients - First Exemplary Embodiment

| Ingredient | Vol. (ml) | % Volume | Wide Variance | General Variance | Desired Variance |
|---|---|---|---|---|---|
| Water | 350 | 58.02 | 0%-90% | 0%-89.9% | 25%-78% |
| Cleaner | 50 | 5.00 | 0%-25% | 5%-15% | 8%-12% |
| Surfactants | 50 | 5.00 | 0%-25% | 5%-15% | 8%-12% |
| Preservative | 2.5 | 0.25 | 0%-4% | 0.1%-1.0% | 0.3%-0.8% |
| Colorant | 0.25 | 0.025 | 0%-4% | 0.01%-0.1% | 0.03%-0.08% |
| Foam boosters | 0.25 | 0.025 | 0%-4% | 0.01%-0.1% | 0.03%-0.08% |
| Thickener | 0.25 | 0.025 | 0%-4% | 0.01%-0.1% | 0.03%-0.08% |
| Total | 453.25 | 100.0 | | | |

Another exemplary dishwashing soap 120 component of the exemplary skin blemish and acne treatment composition 100, including Grapefruit and Green Tea, comprises at least a portion of the following active all natural ingredients:
 a. Water,
 b. Sodium Laureth Sulfate,
 c. Alkyl Poly Glycoside C10-16,
 d. A First Perfume,
 e. A Second Perfume,
 f. Limonene (D-), and
 g. 2-Bromo-2-Nitropropane-1,3-Diol.

TABLE 4

Exemplary Dishwashing Soap Ingredients
Dishwashing Soap Ingredients - Exemplary Embodiment

| Ingredient | Vol. (ml) | % Volume | Wide Variance | General Variance | Desired Variance |
|---|---|---|---|---|---|
| Water | 350 | 58.02 | 0%-90% | 0%-89.9% | 25%-78% |
| Other Ingredients | 150 | 24.87 | 0%-90% | 0%-89.9% | 20%-78% |
| Sodium Laureth Sulfate | 50 | 5.00 | 2%-20% | 5%-15% | 8%-12% |
| Alkyl Poly Glycoside C10-16 | 50 | 5.00 | 2%-20% | 5%-15% | 8%-12% |
| First Perfume | 2.5 | 0.25 | 0%-4% | 0.1%-1.0% | 0.3%-0.8% |
| Second Perfume | 0.25 | 0.025 | 0%-4% | 0.01%-0.1% | 0.03%-0.08% |
| Limonene (D-) | 0.25 | 0.025 | 0%-2% | 0.01%-0.1% | 0.03%-0.08% |
| 2-Bromo-2-Nitropropane-1,3-Diol | 0.25 | 0.025 | 0%-2% | 0.01%-0.1% | 0.03%-0.08% |
| Total | 603.25 | 100.0 | | | |

Another exemplary dishwashing soap 120 component of the exemplary skin blemish and acne treatment composition 100, including Lemon and Aloe Vera, comprises at least a portion of the following active all natural ingredients:
 a. Sodium Lauryl Ether Sulfate,
 b. Fatty Alcohol Sulfate C10-16,
 c. Alkyl Poly Glycoside C10-16,
 d. Alkyl Poly Glycoside C8-10,
 e. Citric Acid,
 f. Perfume,
 g. Limonene (D-), and
 h. Citral.

TABLE 5

Exemplary Dishwashing Soap Ingredients
Dishwashing Soap Ingredients - Exemplary Embodiment

| Ingredient | Vol. (ml) | % Volume | Wide Variance | General Variance | Desired Variance |
|---|---|---|---|---|---|
| Water | 350 | 43.59 | 0%-90% | 0%-89.9% | 25%-78% |
| Other Ingredients | 250 | 31.13 | 0%-90% | 0%-89.9% | 20%-78% |
| Sodium Lauryl Ether Sulfate | 85 | 10.59 | 2%-20% | 5%-15% | 8%-12% |
| Fatty Alcohol Sulfate C10-16 | 85 | 10.59 | 2%-20% | 5%-15% | 8%-12% |
| Alkyl Poly Glycoside C10-16 | 25 | 3.11 | 0.5%-10% | 1%-5% | 2%-4% |
| Alkyl Poly Glycoside C8-10 | 3 | 0.374 | 0%-4% | 0.1%-1.0% | 0.3%-0.8% |
| Citric Acid | 4 | 0.498 | 0%-4% | 0.1%-1.0% | 0.3%-0.8% |
| Perfume | 0.3 | 0.037 | 0%-2% | 0.01%-0.1% | 0.03%-0.08% |
| Limonene (D-) | 0.35 | 0.044 | 0%-2% | 0.01%-0.1% | 0.03%-0.08% |
| Citral | 0.35 | 0.044 | 0%-2% | 0.01%-0.1% | 0.03%-0.08% |

TABLE 5-continued

Exemplary Dishwashing Soap Ingredients
Dishwashing Soap Ingredients - Exemplary Embodiment

| Ingredient | Vol. (ml) | % Volume | Wide Variance | General Variance | Desired Variance |
|---|---|---|---|---|---|
| | | % Volume | | | |
| Total | 803 | 100.0 | | | |

Another exemplary dishwashing soap 120 component of the exemplary skin blemish and acne treatment composition 100 comprises the following ingredients:
 a. oxygen chlorine-free bleach,
 b. plant-based non-ionic tension-active surfactants,
 c. enzymes,
 d. salts,
 e. silicate,
 f. citrate,
 g. polypeptides,
 h. plant based bleach activator, and
 i. plant based fragrance.

Another exemplary dishwashing soap 120 component of the exemplary skin blemish and acne treatment composition 100 comprises the following ingredients:
 a. Water,
 b. Sodium Laureth Sulfate,
 c. Lauryl Polyglucose,
 d. Sodium Chloride,
 e. Citric Acid,
 f. Fragrance,
 g. Limonene,
 h. Hydrolized Wheat Gluten,
 i. Aloe Barbadensis Gel,
 j. Citral, and
 k. 2-bromo-2-nitropropane-1,3-diol.

The skin blemish and acne treatment composition 100 may be commercialized and packaged in any form factor, such as 12 oz, 16 oz, and 24 oz containers and offered as a body wash product for application during showering.

Figure 2:
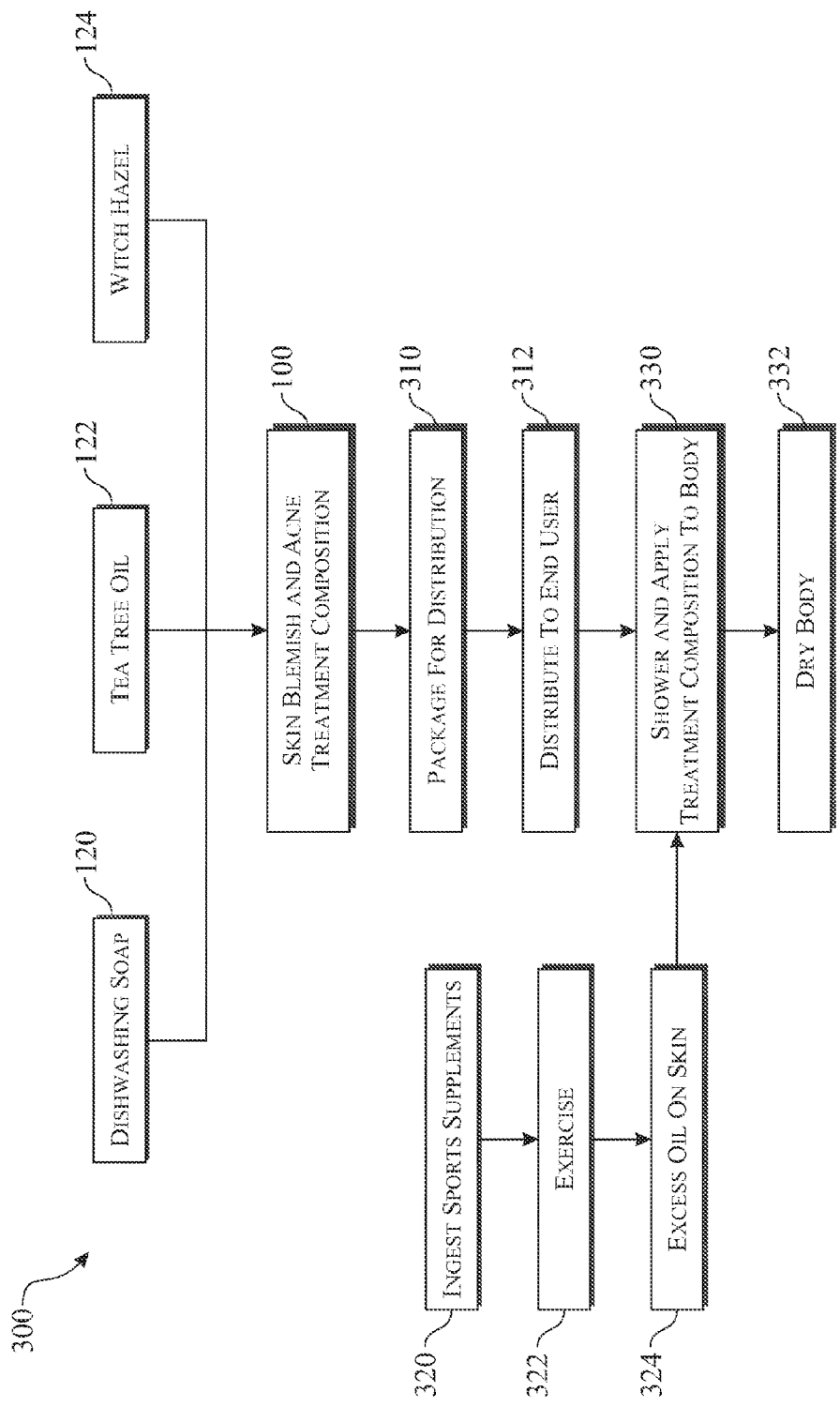
FIG. 2 presents a flow diagram representing a general application of the skin blemish and acne treatment composition.

An exemplary application of the skin blemish and acne treatment composition 100 is illustrated in an acne and skin blemish treatment process flow diagram 300 presented in FIG. 2, while referencing the exemplary isometric demonstration illustrated in FIG. 1. The acne and skin blemish treatment process flow diagram 300 initiates with the mixing of the skin blemish and acne treatment composition 100, by combining the predetermined volume of dishwashing soap 120, the predetermined volume of tea tree oil 122, and the predetermined volume of witch hazel 124. The skin blemish and acne treatment composition 100 is packaged for distribution 310 and distributed through any common distribution channel to an end user 312.

The individual 200 can optionally ingest sports supplements 320. The individual 200 completes one or more exercises 322. The exercise 322 is generally sufficient to generate sweat and excess oil on the skin 324 of the individual 200. The sweat and excess oil on the skin 324 can cause skin blemishes and promotes acne. After exercising, it is common for the individual 200 to bath. Common bath soap is limited where it is not directed to remove excess oil. The common soap also fails to include any ingredient directly targeting to treat acne. The individual 200 would apply the skin blemish and acne treatment composition 100 to the individual's torso 210, the individual's face 212, the individual's arms 214 and individual's legs 216 in accordance with a body wash 330. The individual 200 would continue showering, washing their hair, shaving (as desired), and the like. Upon completion of the bathing process, the individual 200 would dry their body 332 and subsequently dress appropriate for their next function.

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalence.

I claim:

1. A method of treating skin blemishes and acne, the method comprising the steps:
 mixing a predetermined volume of dishwashing soap including castile soap, water, tea tree oil, fresh lemon juice, white vinegar, and witch hazel into a skin blemish and acne treatment composition, wherein the ingredients are provided in the following volumes:
  a. castile soap, comprising 5% to 15% of the total content,
  b. water, comprising 5% to 15% of the total content,
  c. tea tree oil, comprising 5% to 15% of the total content,
  d. fresh lemon juice, comprising 5% to 15% of the total content, and
  e. white vinegar, comprising 5% to 15% of the total content;
 packaging the skin blemish and acne treatment composition into a composition distribution container;
 distributing the composition distribution containers through at least one distribution channel to an individual;
 applying the skin blemish and acne treatment composition to a body of the individual during a showering process.

2. A method of treating skin blemishes and acne as recited in claim 1, the method comprising the step of applying the skin blemish and acne treatment composition to a torso of the individual.

3. A method of treating skin blemishes and acne as recited in claim 1, the method comprising the step of applying the skin blemish and acne treatment composition to extremities of the individual.

4. A method of treating skin blemishes and acne as recited in claim 1, the composition being further refined by limiting the volumes of the ingredients as follows:
 the volume of tea tree oil falling within a range of 5 percent to 10 percent by volume; and
 the volume of witch hazel falling within a range of 0.1 percent to 20 percent by volume.

5. A method of treating skin blemishes and acne as recited in claim 1, the composition being further refined by limiting the volumes of the ingredients as follows:
 the volume of tea tree oil falling within a range of 5 percent to 7.5 percent by volume; and
 the volume of witch hazel falling within a range of 0.5 percent to 10 percent by volume.

6. A method of treating skin blemishes and acne as recited in claim 1, the composition being further refined by limiting the volumes of the ingredients as follows:
 the volume of witch hazel falling within a range of 1.0 percent to 5 percent by volume.

7. A method of treating skin blemishes and acne, the method comprising the steps:
 mixing a predetermined volume of dishwashing soap including castile soap, water, tea tree oil, fresh lemon juice, white vinegar, and witch hazel into a skin blemish and acne treatment composition, wherein the ingredients are provided in the following volumes:
  a. castile soap, comprising 5% to 15% of the total content,
  b. water, comprising 5% to 15% of the total content,
  c. tea tree oil, comprising 5% to 15% of the total content,
  d. fresh lemon juice, comprising 5% to 15% of the total content, and
  e. white vinegar, comprising 5% to 15% of the total content;
the dishwashing soap comprising at least one active ingredients selected from a group of active ingredients consisting of:
  a predetermined volume of sodium lauryl ether sulfate,
  a predetermined volume of sodium laureth sulfate,
  a predetermined volume of fatty alcohol sulfate,
  a predetermined volume of alkyl poly glycoside,
  a predetermined volume of citric acid, and
  a predetermined volume of citral;
packaging the skin blemish and acne treatment composition into a composition distribution container;
distributing the composition distribution containers through at least one distribution channel to an individual;
applying the skin blemish and acne treatment composition to a body of the individual during a showering process.

8. A method of treating skin blemishes and acne as recited in claim 7, the method comprising the step of applying the skin blemish and acne treatment composition to a torso of the individual.

9. A method of treating skin blemishes and acne as recited in claim 7, the method comprising the step of applying the skin blemish and acne treatment composition to extremities of the individual.

10. A method of treating skin blemishes and acne as recited in claim 7, the composition being further refined by limiting the volumes of the ingredients as follows:
  the volume of tea tree oil falling within a range of 5 percent to 10 percent by volume; and
  the volume of witch hazel falling within a range of 0.1 percent to 20 percent by volume.

11. A method of treating skin blemishes and acne as recited in claim 7, the composition being further refined by limiting the volumes of the ingredients as follows:
  the volume of tea tree oil falling within a range of 5 percent to 7.5 percent by volume; and
  the volume of witch hazel falling within a range of 0.5 percent to 10 percent by volume.

12. A method of treating skin blemishes and acne as recited in claim 7, the composition being further refined by limiting the volumes of the ingredients as follows:
  the volume of witch hazel falling within a range of 1.0 percent to 5 percent by volume.

13. A method of treating skin blemishes and acne, the method comprising the steps:
  mixing a predetermined volume of dishwashing soap including castile soap, water, tea tree oil, fresh lemon juice, white vinegar, and witch hazel into a skin blemish and acne treatment composition, wherein the ingredients are provided in the following volumes:
    a. castile soap, comprising 5% to 15% of the total content,
    b. water, comprising 5% to 15% of the total content,
    c. tea tree oil, comprising 5% to 15% of the total content,
    d. fresh lemon juice, comprising 5% to 15% of the total content, and
    e. white vinegar, comprising 5% to 15% of the total content;
  the dishwashing soap comprising at least one active ingredients selected from a group of active ingredients consisting of:
    a predetermined volume of chlorine-free oxygen bleach,
    a predetermined volume of plant-based non-ionic tension-active surfactants,
    a predetermined volume of enzymes,
    a predetermined volume of salts,
    a predetermined volume of silicate,
    a predetermined volume of citrate, and
    a predetermined volume of polypeptides;
  packaging the skin blemish and acne treatment composition into a composition distribution container;
  distributing the composition distribution containers through at least one distribution channel to an individual;
  applying the skin blemish and acne treatment composition to a body of the individual during a showering process.

14. A method of treating skin blemishes and acne as recited in claim 13, the method comprising the step of applying the skin blemish and acne treatment composition to a torso of the individual.

15. A method of treating skin blemishes and acne as recited in claim 13, the method comprising the step of applying the skin blemish and acne treatment composition to extremities of the individual.

16. A method of treating skin blemishes and acne as recited in claim 13, the composition being further refined by limiting the volumes of the ingredients as follows:
  the volume of tea tree oil falling within a range of 5 percent to 10 percent by volume; and
  the volume of witch hazel falling within a range of 0.1 percent to 20 percent by volume.

17. A method of treating skin blemishes and acne as recited in claim 13, the composition being further refined by limiting the volumes of the ingredients as follows:
  the volume of tea tree oil falling within a range of 5 percent to 7.5 percent by volume; and
  the volume of witch hazel falling within a range of 0.5 percent to 10 percent by volume.

18. A method of treating skin blemishes and acne as recited in claim 13, the composition being further refined by limiting the volumes of the ingredients as follows:
  the volume of witch hazel falling within a range of 1.0 percent to 5 percent by volume.

* * * * *